US006284268B1

(12) United States Patent
Mishra et al.

(10) Patent No.: US 6,284,268 B1
(45) Date of Patent: Sep. 4, 2001

(54) PHARMACEUTICAL COMPOSITIONS CONTAINING AN OMEGA-3 FATTY ACID OIL

(75) Inventors: Awadhesh Mishra, Nuns Island; Iskander Moussa, Montreal, both of (CA); Zeibunissa Ramtoola; Nuala Clarke, both of Dublin (IE)

(73) Assignee: Cyclosporine Therapeutics Limited, Dublin (IE)

( * ) Notice: Subject to any disclaimer, the term of this patent is extended or adjusted under 35 U.S.C. 154(b) by 0 days.

(21) Appl. No.: 09/209,066

(22) Filed: Dec. 10, 1998

Related U.S. Application Data

(63) Continuation-in-part of application No. 08/988,270, filed on Dec. 10, 1997, now abandoned.
(60) Provisional application No. 60/084,516, filed on May 7, 1998.

(51) Int. Cl.[7] ............................. A61K 9/10; A61K 9/107; A61K 9/48; A61K 9/66
(52) U.S. Cl. ....................... 424/455; 424/423; 424/443; 424/451; 424/452; 424/456; 514/784; 514/785; 514/786; 514/937; 514/974
(58) Field of Search .................................. 424/450, 455, 424/456, 423, 443, 451, 452

(56) References Cited

U.S. PATENT DOCUMENTS

| | | | |
|---|---|---|---|
| 4,970,076 | * | 11/1990 | Horrobin ............................ 424/456 |
| 4,990,337 | | 2/1991 | Kurihara . |
| 5,342,625 | | 8/1994 | Hauer . |
| 5,364,632 | | 11/1994 | Benita . |
| 5,589,455 | | 12/1996 | Woo . |
| 5,603,951 | * | 2/1997 | Woo ..................................... 424/455 |
| 5,639,474 | | 6/1997 | Woo . |
| 5,639,724 | | 6/1997 | Cavanak . |
| 5,652,212 | | 7/1997 | Cavanak . |

FOREIGN PATENT DOCUMENTS

| | | |
|---|---|---|
| 0 314 060 | 5/1989 | (EP) . |
| 0 589 843 A1 | 3/1994 | (EP) . |
| 0 760 237 A1 | 3/1997 | (EP) . |
| 0 670 715 B1 | 5/1997 | (EP) . |
| 0 539 319 B1 | 12/1999 | (EP) . |
| 2 217 173 | 10/1989 | (GB) . |
| WO 94/08603 | 4/1994 | (WO) . |
| WO 94/08605 | 4/1994 | (WO) . |
| WO 94/23733 | 10/1994 | (WO) . |
| WO 94/25068 | 11/1994 | (WO) . |
| WO 95/11039 | 4/1995 | (WO) . |
| WO 95/33490 | 12/1995 | (WO) . |
| WO 96/13273 | 5/1996 | (WO) . |
| WO 97/00080 | 1/1997 | (WO) . |
| WO 97/02042 | 1/1997 | (WO) . |
| WO 97/12626 | 4/1997 | (WO) . |
| WO 97/19692 | 6/1997 | (WO) . |
| WO 97/22358 | 6/1997 | (WO) . |
| WO 97/25977 | 7/1997 | (WO) . |
| WO 97/26003 | 7/1997 | (WO) . |
| WO 97/36610 | 10/1997 | (WO) . |

* cited by examiner

*Primary Examiner*—James M. Spear
(74) *Attorney, Agent, or Firm*—Dann, Dorfman, Herrell and Skillman; Stephen H. Eland

(57) ABSTRACT

Self-emulsifying microemulsion or emulsion preconcentrate pharmaceutical compositions containing an omega-3 fatty acid oil such as a fish oil and a poorly water soluble therapeutic agent such as cyclosporin are formulated for administration, particularly oral administration to a human. The preconcentrates, which are substantially free of or contain only minor amounts of a hydrophilic solvent system, contain a pharmaceutically effective amount of an omega-3 fatty acid oil; a therapeutically effective amount of a poorly water soluble therapeutic agent that is substantially soluble in the omega-3 fatty acid oil; and a surfactant system comprising at least one surfactant. Microemulsions or emulsions formed by diluting the self-emulsifying preconcentrate with an aqueous solution are also provided.

39 Claims, 2 Drawing Sheets

PHARMACEUTICAL COMPOSITIONS CONTAINING AN OMEGA-3 FATTY ACID OIL

This application claims priority from U.S. Provisional Application 60/084,516, filed May 7, 1998 and is a continuation-in-part of U.S. application Ser. No. 08/988,270, filed Dec. 10, 1997, now abandoned.

FIELD OF THE INVENTION

The present invention relates to pharmaceutical compositions containing an omega-3 fatty acid oil and a therapeutic agent. In particular, the present invention relates to the administration, particularly oral, of self-emulsifying microemulsion and emulsion preconcentrate formulations or microemulsions and emulsions which contain omega-3 fatty acid oil and a poorly water soluble therapeutic agent, for example, cyclosporin. Preferably, the omega-3 fatty acid oil and therapeutic agent exert an additive or synergistic therapeutic effect or the omega-3 fatty acid oil mediates the negative side effects of the therapeutic agent.

BACKGROUND OF THE INVENTION

Omega-3 fatty acid oils possess properties that can be used for numerous therapeutic advantages, including treatment of autoimmune and inflammatory diseases such as rheumatoid arthritis, psoriasis, inflammatory bowel diseases such as Crohn's disease and ulcerative colitis; immunosuppressive treatment; hypertension prophylaxis in normal humans and in heart transplant patients; coronary heart disease; hyperlipidemia; hypertriglyceridemia; improvement of renal function and nephrotoxicity reduction. U.S. Pat. No. 4,678,808 describes the use of these oils to treat disorders associated with arachidonic acid metabolites, including autoimmune syndromes, acute and chronic inflammatory diseases, atherosclerosis, stroke, myocardial infarction, deep vein thrombosis, surgery, hyperlipidaemic states, hypertension, enhanced platelet responsiveness, vascular lesions and occlusions, vascular spasm and diabetes. According to U.S. Pat. No. 5,225,441, which describes compositions for treating gingivitis and periodontitis, omega-3 polyunsaturated fatty acids compete with omega-6 polyunsaturated fatty acids as a substrate in the arachidonic acid cascade and can therefore alter the synthesis of prostaglandin and leukotrienes, both of which are powerful mediators of inflammation and immune response. Other uses of omega-3 fatty acid oils are described in U.S. Pat. No. 5,034,415 (diabetes mellitus), U.S. Pat. No. 4,843,095 (rheumatoid, arthritis), JP 2253629 (anticancer), U.S. Pat. No. 4,879,312 (enhancing angiogenesis), JP 1290625 (improvement of cerebral function), EP 378,824 (anti-cachexia, cholesterol and triglyceride levels reduction, platelet aggregation inhibition, colon adenocarcinomas growth inhibition), U.S. Pat. No. 5,457,130 (cancer cachexia, malignant tumors, abnormal cAMP levels in adipose tissue, lipolytic activity inhibition) and U.S. Pat. No. 5,436,269 (hepatitis).

Cyclosporins are an example of a class of drugs that is soluble in omega-3 fatty acid oil and capable of exerting an additive or synergistic therapeutic effect with the omega-3 fatty acid oil. Alternatively, the omega-3 fatty acid oil mediates the negative side effects, such as nephrotoxicity, of a cyclosporin such as cyclosporin A.

Cyclosporin A (CyA) is a lipophilic cyclic undecapeptide that can be isolated from the fungus Tolypoclodium inflatum Gams and which produces calcium dependent, specific and reversible inhibition of transcription of interleukin-2 and several other cytokines, most notably in T helper lymphocytes. Because of its immunosuppressive properties, it is widely used as first line therapy in the prophylaxis and treatment of transplant rejection (e.g., allo- or xeno-transplant rejection such as in patients receiving heart, lung, combined heart-lung, liver, kidney, pancreatic, skin or corneal transplants) and various autoimmune and inflammatory diseases. CyA is used in the treatment of multi-drug resistance syndrome, for example in patients undergoing chemotherapy or following organ transplantations. In patients with severe disease refractory to standard treatment; CyA is an effective therapy in acute ocular Behcet's syndrome; endogenous uveitis; psoriasis; atopic dermatitis; arthritis, particularly rheumatoid arthritis; active Crohn's disease and nephrotic syndrome. Other conditions include arthritis chronica progrediente and arthritis deformans, autoimmune hematological disorders including hemolytic anemia, aplastic anemia, pure red-cell anemia and idiopathic thrombocytopenia, systemic lupus erythematosus, polychondroitis, scleroderma, Wegener granulamtosis, dermatomyositis, chronic active hepatitis, myasthenia gravis, Steven-John syndrome, idiopathic sprue, autoimmune inflammatory bowel disease, e.g., ulcerative colitis, endocrine ophthalmology, Graves disease, sarcoidosis, multiple sclerosis, primary biliary cirrhosis, juvenile diabetes, keratoconjunctivitis sicca and vernal keratoconjunctivitis, interstitial lung fibrosis, psoriatic arthritis, glomerulonephritis, juvenile dermatitis, asthma, tumors, hyperproliferative skin disorders and fungal infections. This drug has also been used to treat patients with moderate or severe aplastic anemia who are ineligible for bone marrow transplantation and those with primary biliary cirrhosis. CyA may be effective in patients with intractable pyoderma gangrenosum, polymyositis/dermatomyositis or severe, corticosteroid-dependent asthma. CyA is known to have a very specific effect on T-cell proliferation although the precise mechanism remains unclear. A number of non-immunosuppressive analogues of cyclosporin A have been shown to have resistance modifier activity and some are more potent than the parent compound. Nephrotoxicity, hepatotoxicity, hypertension, headache, hypertrichosis, gingival hyperplasia, neurological and gastrointestinal effects, thrombocytopenia and microangiopathic hemolytic anemia, hyperkalemia and hyperuricemia and development of skin and lymphoproliferative malignancies are the most common adverse events in cyclosporin recipients.

CyA and fish oils have been administered concurrently to organ transplant patients in various clinical trials. For instance, Andreassen et al. (JAAC, 29(6): 1324–31 (1997) reported effective hypertention prophylaxis in heart transplant patients who were given cyclosporin A and 4 g of fish oil. Cyclosporin A-treated and fish oil fed renal transplant recipients had improved renal function following a rejection episode (*Transplantation*, 54:257 (1992)). U.S. Pat. No. 5,118,493 describes the administration of CyA together with an omega-3 fatty acid oil to mediate the nephrotoxic effects of the cyclosporin.

Certain oil mixtures of lipophilic drugs such as a cyclosporin with vegetable oils or other lipidic substances, surface active agents, solvents and other excipients are known to spontaneously produce dispersions of very low mean particle size (such as<200 nm) when mixed with an aqueous medium. These dispersions are known as microemulsions and the oily mixtures that produce the microemulsions are popularly referred to as microemulsion preconcentrates. Upon oral delivery, the microemulsion preconcentrates are thought to produce similar dispersions of very low particle size with gastric and other physiological fluids.

Cyclosporins are highly lipophilic, poorly water soluble and, therefore, have been supplied as an olive oil or peanut oil solution for clinical use. However, the bioavailability of cyclosporin from such oily solutions is very low and gives rise to great intersubject variation with reported systemic availability ranging from 4 to 25% (Takada, K. et al, *J. Pharmacobio-Dyn.*, 11:80–7 (1988)). The bioavailability of cyclosporin has been reported to be dependent on food, bile and other interacting factors (*Clin. Pharmacokinetics*, 24:472–95 (1993)). A widely used commercial formulation of CyA, SANDIMMUNE® for oral administration, is a solution of cyclosporin A in vegetable oil derivatives containing some other inactive excipients. Very high inter- and intra-patient and food dependent variability in the bioavailability of CyA has been observed from this formulation. The commercial microemulsion preconcentrate formulation, NEORAL®, has been claimed to provide high bioavailability for CyA with low inter-and intra-patient variability. However, risks of adverse drug reactions have been indicated on switching to Neoral® (see, e.g., *Drug Saf*, 16:366–73 (1996); Lancet, 348:205 (1996)).

Numerous microemulsion preconcentrate formulations are known, including soft gel formulations, for enhancing the solubilization and oral bioavailability of a poorly water soluble drug compound such as cyclosporine. Typically, these formulations include an active agent, an oil component, a surfactant to emulsify the formulation and a hydrophilic solvent/co-surfactant system to solubilize the active agent. Typical solvent/co-surfactant systems include ethanol, polyethylene glycols, propylene carbonate, dimethylisosorbide, Transcutol and/or Glycofurol. Disadvantages of these formulations include stability or precipitation problems caused by migration of volatile hydrophilic solvents or cosolvents (e.g., ethanol can permeate a gelatin shell at normal storage temperatures), stability or precipitation problems caused by hygroscopic solvents or co-surfactants (e.g., propylene glycols, Transcutol, Glycofurol), and toxicity problems caused by addition of certain solvents or co-surfactants (e.g., dimethylisosorbide).

Typically, the oil component of a conventional microemulsion consists of fatty acid mono-, di- or triglycerides from a vegetable oil; medium chain triglycerides and/or mono- or di-glycerides; mixtures of glycerides and polygycolized glycerides; tocol, tocopherols, and/or tocotrienols; or hydrophobic alcohols. U.S. Pat. No. 5,603,951 describes a microemulsion concentrate containing cyclosporin as an active ingredient, dimethylisosorbide as a required co-surfactant, a surfactant, and an oil which can be refined fish oil, these components being present in the ratio of 1:1–5:2–10:1–5. The inventors of the '951 patent added dimethylisosorbide, which is a solvent available under the Tradename ARLASOVE®, to the formulation to address the disadvantages listed above for prior solvents/co-surfactants systems such as ethanol, Transcutol, or Glycofurol. The '951 preconcentrates are formed by dissolving the cyclosporin in the dimethylisosorbide at a temperature of approximately 60° C. followed by addition of the oil component and the surfactant.

It is an object of the present invention to provide a stable, self-emulsifying microemulsion or emulsion preconcentrate formulation and/or a microemulsion or emulsion containing an omega-3 fatty acid oil that is capable of enhancing the bioavailability of a poorly water soluble therapeutic agent while minimizing the inter- and intra-patient or food variability in the bioavailability of the therapeutic agent. A further object is to provide self-emulsifying preconcentrates or corresponding microemulsions and emulsions having increased therapeutic agent dosing reproducibility compared to conventional formulations. An additional object is to provide self-emulsifying preconcentrates or corresponding microemulsions or emulsions containing an omega-3 fatty acid oil and a poorly water soluble therapeutic agent in which the bioavailability and dosing reproducibility of both the omega-3 fatty acid oil and the therapeutic agent is high.

It is an additional object of this invention to provide a stable self-emulsifying microemulsion or emulsion preconcentrate formulation and/or a microemulsion or emulsion in which the omega-3 fatty acid oil and the therapeutic agent exert an additive or synergistic therapeutic effect or the omega-3 fatty acid oil mediates the negative side effects of the therapeutic agent.

A further object of this invention is to provide a stable self-emulsifying preconcentrates and/or a microemulsion or emulsion in which the poorly water soluble therapeutic agent is substantially soluble in the omega-3 fatty acid oil, thus eliminating or drastically reducing the need for substantial amounts of a hydrophilic solvent system.

A further object of this invention is to provide a stable self-emulsifying microemulsion or emulsion preconcentrate formulation and/or a microemulsion or emulsion containing an omega-3 fatty acid oil and a poorly water soluble therapeutic agent which is suitable for formulation into soft or hard capsules for oral administration.

A still further object of this invention is to provide a stable self-emulsifying microemulsion or emulsion preconcentrate soft or hard capsule formulation containing an omega-3 fatty acid oil and a poorly water soluble therapeutic agent having relatively high therapeutic amounts of both the omega-3 fatty acid oil and the poorly water soluble therapeutic agent.

SUMMARY OF THE INVENTION

Surprisingly, it has been found that stable, self-emulsifying microemulsion or emulsion preconcentrates comprising a poorly water soluble drug can be formed using an omega-3 fatty acid oil to substantially solubilize the poorly water soluble drug. The solubilizing properties of the omega-3 fatty acid oil eliminate or drastically reduce the need for substantial amounts of a hydrophilic solvent/co-solvent system, also allowing for formulation of preconcentrates that are substantially free of a hydrophilic solvent/co-solvent system or contain only minor amounts of a hydrophilic solvent/co-solvent system. It was also found that the solubility of a poorly water soluble drug was enhanced in oils containing a mixture of omega-3 fatty acid oils, thus allowing formulation of preconcentrates containing relatively higher quantities of the poorly water soluble drug. The self-emulsifying microemulsion and emulsion preconcentrates according to the instant invention take the form of a poorly water soluble therapeutic agent substantially solubilized in an omega-3 fatty acid oil that is capable of being self-emulsified by a surfactant system comprising at least one surfactant when the preconcentrate is diluted with an aqueous medium.

Thus, the present invention provides a self-emulsifying preconcentrate pharmaceutical composition suitable for administration to a mammal, particularly oral administration to a human, and capable of forming an oil-in-water microemulsion or emulsion upon dilution with an aqueous solution, comprising (a) a pharmaceutically effective amount of an omega-3 fatty acid oil;

(b) a therapeutically effective amount of a poorly water soluble therapeutic agent, wherein the poorly water soluble therapeutic agent is substantially soluble in the omega-3 fatty acid oil; and (c) a surfactant system comprising at least one surfactant; wherein the composition contains minor amounts or is substantially free of a hydrophilic solvent system. The present invention also provides microemulsions or emulsions formed by diluting a self-emulsifying preconcentrate with an aqueous solution.

Compositions according to this invention that are substantially free or contain only minor amounts of a hydrophilic solvent system avoid the disadvantages of the prior art systems given above.

The therapeutic agent, which is substantially soluble in the omega-3 fatty acid oil, is beneficially co-administered with the omega-3 fatty acid oil to achieve, for instance, greater bioavailability or less variation in the bioavailability of the therapeutic agent, an additive therapeutic effect with the omega-3 fatty acid oil, a synergistic therapeutic effect with the omega-3 fatty acid oil, or a reduction in at least one side effect of the therapeutic agent. Thus, the present invention also encompasses methods for lowering the therapeutically effective amount of a poorly water soluble therapeutic agent by administering to a human in need of a therapeutically effective amount of the therapeutic agent the self-emulsifying preconcentrates or the microemulsions/emulsions of the present invention. Further, the present invention encompasses methods for reducing the side effects of a poorly water soluble therapeutic agent by administering to a human in need of a therapeutically effective amount of the therapeutic agent the self-emulsifying preconcentrates or the microemulsions/emulsion of the present invention.

A preferred therapeutic agent is a cyclosporin, particularly cyclosporin A. Preferred omega-3 fatty acid oils include omega-3 free fatty acids, omega-3 fatty acid triglycerides and omega-3 fatty acid ethyl esters, such as EPA, DHA, triglycerides of EPA, triglycerides of DHA, ethyl esters of EPA, ethyl esters of DHA and mixtures thereof.

Oils containing high concentrations of omega-3 fatty acid oils such as fish oils or their mixtures are particularly useful for forming self-emulsifying preconcentrates, microemulsions or emulsions according to the present invention. Preferably, the oil is fish oil containing at least 50%, preferably at least 70%, more preferably at least 80% omega-3 fatty acid oil to obtain a pharmaceutically effective amount of an omega-3 fatty acid oil in a minimal volume. Because of the solubility of the therapeutic agent in the oil or mixture of oils containing omega-3 fatty acid oil, self-emulsifying preconcentrate, microemulsion or emulsion compositions containing both a therapeutically effective amount of the therapeutic agent and an amount of omega-3 fatty acid oil needed to achieve beneficial co-administration with the therapeutic agent can be formulated with minimal added excipients.

DETAILED DESCRIPTION OF THE INVENTION

Figure 1:
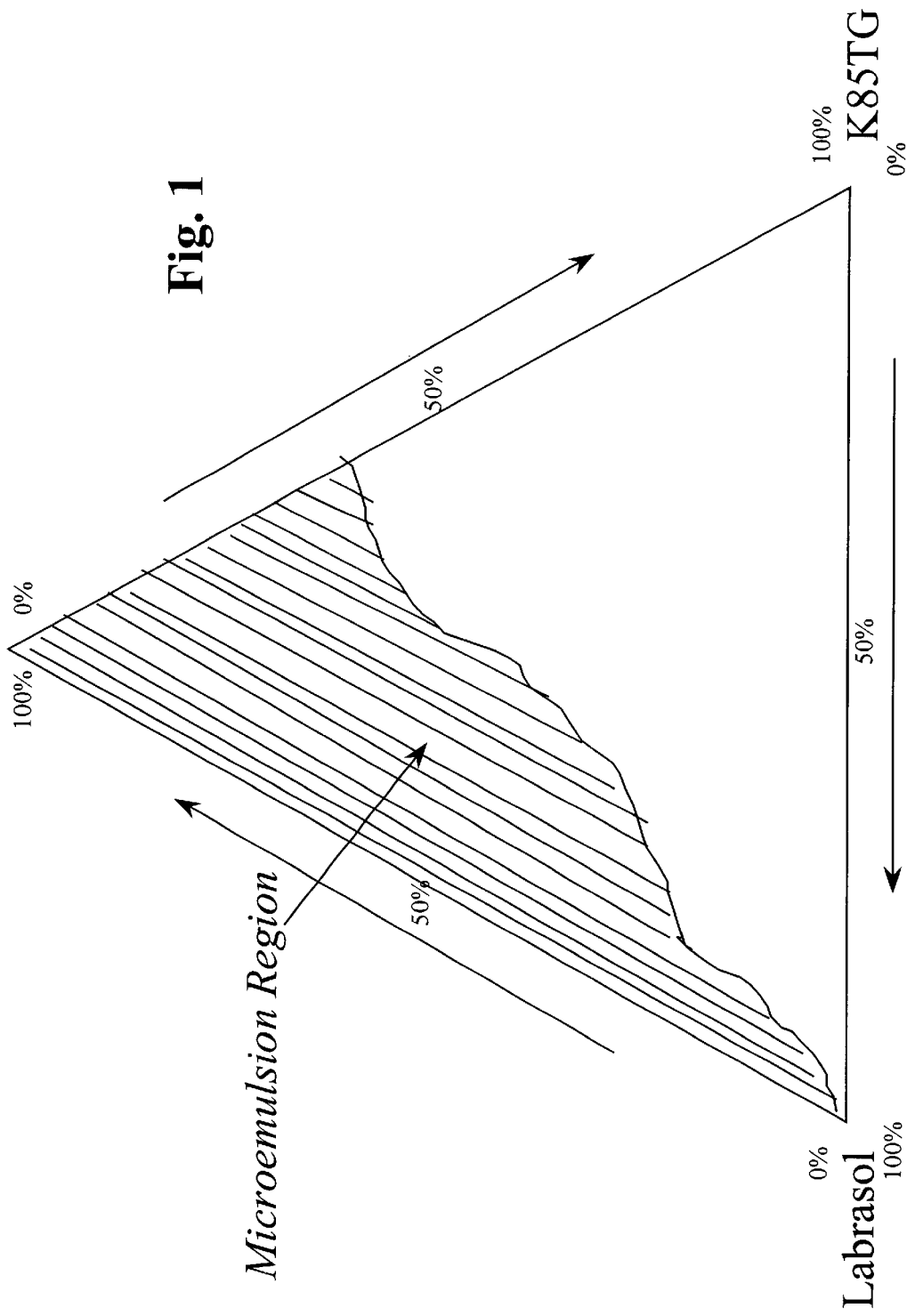
FIG. 1 shows a pseudo-ternary phase diagram for the placebo system described in Example 8 upon a 1 to 20 dilution of the preconcentrate with water. The diagram plots the relative concentration of Labrasol (0 to 100%), the concentration of the omega-3 fatty acid oil K85TG (0 to 100%), and the concentration of Cremophor RH40: Tween 80 in a 2:1 ratio (0 to 100%) for the placebo system. The relative concentration of Labrasol increases from 0% at the lower right hand margin of the diagram to 100% at the lower left corner; the relative concentration of Cremophor RH40: Tween 80 in a 2:1 ratio increases from 0% at the baseline of the diagram to 100% at the apex; and the relative concentration of K85TG increases from 0% at the apex to 100% at the lower right hand corner of the diagram. The shaded area identifies those compositions having C1, C1/C2 or C2 clarity as the microemulsion region for a 1 to 20 dilution of the preconcentrate with water.

As used herein, the term "omega-3 fatty acid oil" means a natural or synthetic omega-3 fatty acid, and pharmaceutically acceptable esters, derivatives, precursors or salts thereof and mixtures thereof. Examples of omega-3 fatty acid oils include but are not limited to omega-3 polyunsaturated, long-chain fatty acids such as a eicosapenta-5,8,11,14,17-enoic acid (hereinafter "EPA"), docosahexa-4,7,10,13,16,19-enoic acid (hereinafter "DHA"), and α-linolenic acid; esters of an omega-3 fatty acid with glycerol such as mono-, di- and triglycerides; esters of the omega-3 fatty acid and a primary alcohol such as fatty acid methyl esters and fatty acid ethyl esters; precursors of an omega-3 fatty acid oil, such as EPA and DHA precursor α-linolenic acid; and derivatives such as polyglycolized derivatives or polyoxyethylene derivatives. Preferred omega-3 fatty acid oils are EPA or DHA, triglycerides thereof, ethyl esters thereof and mixtures thereof. The omega-3 fatty acids or their esters, derivatives, precursors, salts and mixtures thereof can be used either in their pure form or as a component of an oil such as fish oil (otherwise known as marine oil), preferably highly purified fish oil concentrates, or perilla oil or marine microalgae oil. Suitable fish oils are, for example, those types which are recovered in substantial quantities from cold-water fish, such as pilchard oil, menhaden oil, Peruvian fish oil, sardine oil, salmon oil, herring oil, and mackerel oil. Preferably, the fish oil has a high omega-3 fatty acid oil content, such as 50% or higher, more preferably, 70% or higher, most preferably 80% or higher. Examples of suitable omega-3 fatty acid oils include the following oils available from Croda Oleochemicals (England): Incromega TG3525 (35:25 EPA:DHA ratio; triglycerides), Incromega E5015 (50:15 EPA:DHA ratio; ethyl esters) and the following oils available from Pronova Biocare (Sandefjord, Norway): EPAX6000FA, EPAX5000TG, EPAX4510TG, EPAX2050TG, K85TG, K85EE, K80EE and EPAX7010EE (further details listed in Table 1 herein). Preferred mixtures include mixtures of fatty acid ethyl esters and fatty acids; fatty acid ethyl esters and fatty acid triglycerides; fatty acids and fatty acid triglycerides; and fatty acid esters, fatty acid triglycerides and fatty acids such as mixtures containing K85EE and EPAX6000FA; EPAX5000TG and EPAX6000FA; K85EE and EPAX5000TG; and K85EE, EPAX6000FA and EPAX5000TG.

As used herein, the term "therapeutic agent" means a poorly water soluble drug or a mixture of poorly water soluble drugs that can be beneficially co-administered with an omega-3 fatty acid oil to a mammal, especially a human. By "poorly water soluble drug" is meant a drug that is insoluble in water or has an aqueous solubility of less than about 5 part per 1000 parts of water by weight at 20° C. Examples of beneficial co-administration include co-administration that results in at least one synergistic therapeutic effect or at least one additive therapeutic effect between the therapeutic agent and the omega-3 fatty acid oil; co-administration in which the omega-3 fatty acid oil mediates at least one negative side effect of the therapeutic agent and co-administration in which the omega-3 fatty acid oil solubilizes the therapeutic agent to allow for greater bioavailability and/or reduced variation in the bioavailability of the therapeutic agent. For instance, in addition to other beneficial co-administration effects, omega-3 fatty acid oil reduces the nephrotoxicity of cyclosporin when co-administered, allowing treatment with higher levels of cyclosporin and producing a greater clinical response at a given dose of cyclosporin.

Examples of therapeutic agents include nephrotoxic drugs such as cyclosporins and amphotericin B; cardiotoxic drugs such as amphotericin B and FK506; drugs with immuno-suppressive effects or anti-inflammatory drugs such as drugs for treating rheumatology, arthritis, psoriasis, inflammatory bowel disease, Crohn's disease or demyelinating diseases including multiple sclerosis; anti-tumor drugs such as melphalan, chlormethine, extramustinephosphate, uramustine, ifosfamide, mannomustine, trifosfamide, streptozotocin, mitobronitol, methotrexate, fluorouracil, cytarabine, tegafur, idoxide, taxol, paclitaxel, daunomycin, daunorubicin, bleomycin, amphotericin; hyperlipidemia or hypercholestolemia drugs such as fenofibrate; dioplar disease drugs; drugs which increase lipids and/or triglyceride levels; and drugs for treating Alzheimer's disease. The therapeutic agent can be selected from a variety of known classes of drugs including, but not limited to, analgesics, anti-allergic agents, anti-fungals, anti-inflammatory agents, anti-arrythmic agents, antibiotics, anticoagulants, antidepressants, antidiabetic agents, anti-epilepsy agents, antihypertensive agents, anti-gout agents, anti-malarials, anti-migraine agents, antimuscarinic agents, antineoplastic agents, anti-protozoal agents, anxiolytics, thyroids, anti-thyroids, antivirals, anoretics, bisphosphonates, cardiac inotropic agents, cardiovascular agents, corticosteroids, diuretics, dopaminergic agents, gastrointestinal agents, hemostatics, histamine receptor antagonists, hypnotics, immunosuppressants, kidney protective agents, lipid regulating agents, muscle relaxants, neuroleptics, neurotropic agents, opioid agonists and antagonists, parasympathomimetics, protease inhibitors, prostglandins, sedatives, sex hormones, stimulants, sympathomimetics, vasodilators and xanthins. The therapeutic agent may comprise a mixture of poorly water-soluble drugs that can be beneficially co-administered with an omega-3 fatty acid oil.

As used herein, the term "a pharmaceutically effective amount of an omega-3 fatty acid oil" means an amount effective either 1) to solubilize a therapeutically effective unit dose amount of the poorly water soluble therapeutic agent; 2) to exert an additive therapeutic effect in combination with the poorly water soluble therapeutic agent; 3) to exert a synergistic therapeutic effect in combination with the poorly water soluble therapeutic agent; or 4) to mediate, such as decrease, at least one negative side effect of the therapeutic agent. Typically, the amount of omega-3 fatty acid oil in a unit dose of the self-emulsifying microemulsion or emulsion preconcentrate and/or microemulsion or emulsion can be adjusted so that the daily dose of the omega-3 fatty acid oil is from about 1.0 g to about 6.0 g in humans per day, preferably from about 2.0 g to about 5.0 g, most preferably about 2.5 g to about 4.0 g per day. Alternatively, the typical dosage of the omega-3 fatty acid oil ranges from about 14 to 86 mg/kg/day; the typical dosage of a fish oil contains an equivalent amount of omega-3 fatty acid oil. Preferably, the unit dose amount for an oil containing the omega-3 fatty acid oil ranges from about 5% to 70% of the microemulsion or emulsion preconcentrate.

As used herein, the term "surfactant" means a non-ionic or ionic surfactant having an HLB less than about 20. Suitable surfactants include but are not limited to polyoxyethylene glycolated natural or hydrogenated vegetable oils; polyoxyethylene sorbitan fatty acid esters; polyoxyethylene fatty acid esters; polyoxyethylene alkyl ethers; polyethylene glycol mono- and di- fatty acid esters; transesterification product of natural vegetable oil triglyceride with polyalkylene polyol; and fatty alcohol ethoxylates. Examples of suitable surfactants include Cremophor-RH40, Cremophor-RH60, Cremophor-EL, Tween-20, Tween-40, Tween-60, Tween-65, Tween-80, Tween-85, Labrasol, Nikkol HCO-50, Nikkol HCO-40, Nikkol HCO-60, Brij 30, Gelucire 44/14, Gycerox 767, lmwitor 742, lmwitor 308, lmwitor 375, Labrafac Lipophile, Labrafac CM10, Tagat TO, Myrj 52, Myvacet 9-45, and Vitamin E-TPGS.

As used herein, the term "substantially soluble" in reference to the solubility of the poorly water soluble therapeutic agent in the omega-3 fatty acid oil means the poorly water soluble therapeutic agent is soluble in the omega-3 fatty acid oil or has a solubility of more than 1 part per 100 parts of omega-3 fatty acid oil by weight at 20° C.

As used herein, the term "hydrophilic solvent system" means a system comprising a solvent or co-solvent (other than an omega-3 fatty acid oil) with respect to the poorly water soluble therapeutic agent and/or a co-surfactant having an HLB greater than about 20. Example hydrophilic solvent system components include ethanol, alkylene glycols such as propylene glycol, polyethylene glycol, polyoxypropylene block copolymers, Glycofurol, Transcutol, dimethylisosorbide and mixtures thereof. Preferred hydrophilic solvent system components are 1,2-propylene glycol, ethanol and polyethylene glycol having an average molecular weight of less than or equal to 1000, individually or in combination. More preferred hydrophilic solvent system components are 1,2-propylene glycol and ethanol, individually or in combination. As used herein, the term "minor amounts" as used in reference to a hydrophilic solvent system means an amount less than about 10% by weight of the components present in the preconcentrate, preferably less than about 5% by weight, most preferably less than the amount of therapeutic agent present in the formulation.

The self-emulsifying microemulsion and emulsion preconcentrate and microemulsion and emulsion formulations according to the present invention may optionally include minor amounts of a hydrophilic solvent system to increase the shelf life or stability of the preconcentrates. Other additives, such as antioxidants or preservatives, may also be present. Examples include tocopherol, tocopherols excipient, ascorbyl palmitate, butylated hydroxyanisol or other antioxidants and preservatives listed in USP XXII, Pharmaceutic Ingredients.

The self-emulsifying preconcentrates and the microemulsions and emulsions of the instant invention can be adapted for oral administration. Preferred oral dosage forms for the preconcentrates include hard and softgel capsules. Preformed microemulsions and emulsions are preferred oral dosage forms for the microemulsions and emulsions. The formulations according to the instant invention can also be administered by other routes of administration, including topical administration or parenteral administration such as i.v. or i.p. administration.

EXAMPLE 1
Solubility of Cyclosporin in Fish Oils at Ambient Temperature

The solubility at ambient temperature for cyclosporin A (CyA) was determined at ambient temperature for fish oils containing polyunsaturated omega-3 free fatty acid oil as free fatty acids (EPAX6000FA), omega-3 fatty acid glycerides (EPAX5000TG, EPAX4510TG, EPAX2050TG, and K85TG), omega-3 fatty acid ethyl esters (K85EE, EPAX7010OEE and K80EE) and in a mixture of free fatty acids and ethyl esters (EPAX6000FA/K85EE) (Pronova Biocare, Sandefjord, Norway). The K85TG is a mixed glyceride form obtained by transesterification of K85EE with glycerol giving the resulting blend: K85 monoglyceride: 5–15%; K85 diglyceride: 20–30%; K85 triglyceride: 50–70% and K85EE remnants:<5%. Further details regarding these omega-3 fatty acid oils and the CyA solubilities are given in Table 1.

The solubility of CyA in various oils was found to be variable. A blend of K85EE with EPAX6000FA increased the solubilizing power for CyA greatly compared to either omega-3 fatty acid oil by itself. Furthermore, this CyA solution in a mixture of K85EE and EPAX 6000 remained in the form of a clear solution at low and high temperatures, such as 2–8° C. and about 40° C. No precipitation or crystallization occurred upon cooling to about –20° C. for more than 24 hours. Thus, these initial findings indicate that CyA microemulsion preconcentrates made with this fish oil blend might have very good thermal stability over a wide temperature range.

EXAMPLE 2
Preparation of Microemulsion/Emulsion Preconcentrates

To make the preconcentrate formulations, a solution containing the poorly water soluble therapeutic agent and the oil component containing the omega-3 fatty acid oil were prepared in appropriate proportions by adding is the therapeutic agent in small increments and stirring. The surfactant system was prepared by mixing separately the chosen surfactants in their determined ratios. The oil component/ therapeutic agent solution was then combined with the surfactant system solution to form the preconcentrate, with stirring for approximately 5 minutes with or without heating to 30–40° C. until homogeneous. Alternatively, formulations according to the instant invention were prepared by simply combining the given amounts of the therapeutic agent, the given amounts of the oil component and the given amounts of the surfactant system with stirring until a homogeneous solution was formed. Alternatively, the therapeutic agent can be added to a mixture of the oil component and the surfactant system and stirred until a homogeneous solution was formed. To test the behavior of the preconcentrates upon contact with an aqueous system, the preconcentrate was diluted, such as 1:1, 1:10, 1:20, 1:50 or 1:100 v/v dilutions, with water to simulate conditions in the stomach.

As given in the examples below, a variety of surfactant systems were combined with various omega-3 fatty acid oils at varying ratios of the components and the resulting solutions were diluted 1:20 to determine the component ratios that provide suitable microemulsion and emulsion preconcentrate formulations. Clarity of the resulting solutions was classified as follows: C1 denotes a transparent solution; C2 denotes a translucent solution; C3 denotes a slightly opaque solution; and C4 denotes a milky white solution. Generally, the self-emulsifying microemulsion systems correspond to the C1 to C2 solutions and the self-emulsifying emulsion

TABLE 1

| Fish Oil | Chemical Form | ω-3 content % | EPA % | DHA % | EPA to DHA ratio | Additives mg/g | Solubility mg CyA per g solvent |
|---|---|---|---|---|---|---|---|
| EPAX6000FA | free fatty acid | 55–60 | 33 | 22 | 3:2 | Vit A: 1 IU<br>Vit D: 1 IU<br>Vit E: 3–4.5 | 557 mg/g |
| EPAX5000TG | glycerides | 50 | 30 | 20 | 3:2 | Vit E: 3.0–4.5 | 584 mg/g |
| EPAX4510TG | glycerides | 55 | 45 | 10 | 9:2 | Vit E: min 3.0 | 443 mg/g |
| EPAX2050TG | glycerides | 70 | 20 | 50 | 2:5 | | 459 mg/g |
| K85TG | glycerides | 80 | 45.9 | 33.3 | 1.38:1 | Vit E: 4.0 | 366 mg/g |
| K85EE | ethyl ester | 84 | 46 | 38 | 1.2:1 | Vit E: 3.2–4.8 | 225 mg/g |
| K80EE | ethyl ester | 81 | 45 | 36 | 1:0.8 | Vit E: 3.2–4.8 | |
| EPAX7010EE | ethyl ester | 82 | 70 | 12 | 5.8:1 | Vit E: 2.1–3.2 | 265 mg/g |
| K85EE + EPAX6000FA (2:1 w/w) | ethyl ester + free fatty acid | 73–76 | | | ~3:2 | | 731 mg/g | systems correspond to the C3 to C4 solutions. A pseudo-ternary phase diagram that maps the different clarity regions for a particular omega-3 fatty acid oil/surfactant system can be made to visualize the appropriate ratios of the components needed to form a microemulsion preconcentrate or an emulsion preconcentrate formulation.

EXAMPLE 3
K85EE/Cremophor RH40/Labrasol

Samples were prepared according to Example 2 for the omega-3 fatty acid oil K85EE and a surfactant system comprising Labrasol and Cremophor RH40 with varying percentages for all three of these components. Table 2 charts the clarity values for this system (placebo) upon 1 to 20 dilution with water while Table 3 charts 1 to 20 dilution clarity values for the corresponding systems in which 25, 50, 100 and 150 mg of CyA per ml of solution were added. From an analysis of the placebo system, it appears that the greatest amount of oil possible in a microemulsion preconcentrate formulation formulated according to this system is around 40–45% K85EE.

TABLE 2

| K85EE % | Labrasol % | Cremophor RH40 % | CyA mg/ml | Clarity |
|---|---|---|---|---|
| 5 | 62 | 33 | n/a | C1 |
| 10 | 15 | 75 | n/a | C1 |
| 12 | 45 | 43 | n/a | C1 |
| 15 | 79 | 6 | n/a | C4 |
| 20 | 38 | 42 | n/a | C1/C2 |
| 22 | 65 | 13 | n/a | C4 |
| 27 | 20 | 53 | n/a | C1/C2 |
| 30 | 56 | 14 | n/a | C4 |
| 40 | 10 | 50 | n/a | C2 |
| 50 | 5 | 45 | n/a | C4 |
| 55 | 10 | 35 | n/a | C4 |

TABLE 3

| K85EE % | Labrasol % | Cremophor RH40 % | CyA mg/ml | Clarity |
|---|---|---|---|---|
| 5 | 62 | 33 | 25 | C1 |
| 10 | 15 | 75 | 25 | C1 |
| 12 | 45 | 43 | 25 | C1 |
| 20 | 38 | 42 | 25 | C1 |
| 5 | 62 | 33 | 50 | C1 |
| 10 | 15 | 76 | 50 | C1 |
| 12 | 45 | 43 | 50 | C1 |
| 20 | 38 | 42 | 50 | C1 |
| 5 | 62 | 33 | 100 | C3 |
| 12 | 45 | 43 | 100 | C1 |
| 20 | 38 | 42 | 100 | C1 |
| 5 | 62 | 33 | 150 | C4 |
| 12 | 45 | 43 | 150 | C3 |
| 20 | 38 | 42 | 150 | C2/C3 |

EXAMPLE 4
K85EE/Tween 80/Labrasol

Samples were prepared according to Example 2 for the omega-3 fatty acid oil K85EE a nd a surfactant system comprising Labrasol and Tween 80 with varying percentages for all three of these components. Table 4 charts the clarity values upon 1 to 20 dilution with water for this system (placebo) while Table 5 charts the 1 to 20 dilution clarity values for corresponding systems in which 25 and 50 mg of CyA per ml of solution were added.

TABLE 4

| KE85EE % | Labrasol % | Tween 80 % | CyA mg/ml | Clarity |
|---|---|---|---|---|
| 5 | 62 | 33 | n/a | C1 |
| 10 | 15 | 75 | n/a | C1 |
| 12 | 45 | 43 | n/a | C1/C2 |
| 15 | 79 | 6 | n/a | C4 |
| 20 | 38 | 42 | n/a | C1/C2 |
| 22 | 55 | 13 | n/a | C4 |
| 27 | 20 | 53 | n/a | C1/C2 |
| 30 | 56 | 14 | n/a | C4 |
| 40 | 5 | 55 | n/a | C2/C3 |
| 50 | 5 | 45 | n/a | C2/C3 |
| 53 | 12 | 35 | n/a | C4 |

TABLE 5

| K85EE % | Labrasol % | Tween 80% | CyA mg/ml | Clarity |
|---|---|---|---|---|
| 5 | 62 | 33 | 25 | C2 |
| 10 | 15 | 75 | 25 | C1 |
| 12 | 45 | 43 | 25 | C1/C2 |
| 20 | 38 | 42 | 25 | C2 |
| 27 | 53 | 20 | 25 | C2 |
| 40 | 5 | 55 | 25 | C2/C3 |
| 50 | 5 | 45 | 25 | C4 |
| 5 | 62 | 33 | 50 | C4 |
| 10 | 15 | 75 | 50 | C1/C2 |
| 12 | 45 | 43 | 50 | C2/C3 |
| 20 | 38 | 42 | 50 | C3 |
| 27 | 53 | 20 | 50 | C2/C3 |

Comparison between the K85EE/Cremophor RH40/Labrasol system of Example 3 and the K85EE/Tween 80/Labrasol system of Example 4 shows that while the placebo systems are similar, as cyclosporin is added to the system, the K85EE/Cremophor RH40/Labrasol system provides a larger microemulsion region when plotted on a pseudo-ternary phase diagram.

EXAMPLE 5
K85EE/Cremophor RH40/Tween 80/Labrasol

Samples were prepared according to Example 2 for the omega-3 fatty acid oil K85EE and a surfactant system comprising Labrasol, Tween 80 and Cremophor RH40 (holding the ratio of Cremophor RH40 to Tween 80 at 2:1) with varying percentages of K85EE, Labrasol and Tween 80/Cremophor RH40. Table 6 charts the 1 to 20 dilution clarity values for this system (placebo) as well as the corresponding system with 5% Ethanol included. Table 7 charts 1 to 20 dilution clarity values for corresponding systems in which 100 mg of CyA per ml of solution has been added.

TABLE 6

| K85EE % | Labrasol % | Cremophor RH40:Tween 80 (2:1) % | Ethanol % | CyA mg/ml | Clarity |
|---|---|---|---|---|---|
| 21.7 | 0 | 78.3 | n/a | n/a | C1 |
| 21.7 | 12.6 | 66.7 | n/a | n/a | C1 |
| 21.7 | 20.8 | 67.5 | n/a | n/a | C1 |
| 31 | 0 | 69 | n/a | n/a | C1/C2 |
| 31 | 11 | 68 | n/a | n/a | C1/C2 |
| 31 | 18.4 | 60.6 | n/a | n/a | C1/C2 |
| 38.8 | 0 | 61.2 | n/a | n/a | C1/C2 |
| 38.8 | 9.9 | 51.5 | n/a | n/a | C1/C2 |
| 38.8 | 16.2 | 48 | n/a | n/a | C1/C2 |
| 42.5 | 10.5 | 47 | n/a | n/a | C1/C2 |
| 44 | 5 | 51 | n/a | n/a | C2 |
| 48.5 | 0 | 51.3 | n/a | n/a | C2 |
| 48.5 | 8.2 | 43.3 | n/a | n/a | C2 |
| 48.5 | 13.7 | 37.8 | n/a | n/a | C2 |
| 21.7 | 0 | 78.3 | 5% | n/a | C1 |

TABLE 6-continued

| K85EE % | Labrasol % | Cremophor RH40:Tween 80 (2:1) % | Ethanol % | CyA mg/ml | Clarity |
|---|---|---|---|---|---|
| 21.7 | 12.6 | 66.7 | 5% | n/a | C1 |
| 21.7 | 20.8 | 67.5 | 5% | n/a | C1 |
| 31 | 0 | 69 | 5% | n/a | C1/C2 |
| 31 | 11 | 68 | 5% | n/a | C1/C2 |
| 31 | 18.4 | 60.6 | 5% | n/a | C1/C2 |
| 38.8 | 0 | 61.2 | 5% | n/a | C1/C2 |
| 38.8 | 9.9 | 51.3 | 5% | n/a | C1/C2 |
| 42.5 | 10 | 47.5 | 5% | n/a | C1/C2 |
| 44 | 5 | 51 | 5% | n/a | C1/C2 |
| 48.5 | 0 | 51.5 | 5% | n/a | C1/C2 |
| 48.5 | 8.2 | 43.3 | 5% | n/a | C2 |
| 48.5 | 13.7 | 37.8 | 5% | n/a | C2 |
| 52.5 | 5 | 42.5 | 5% | n/a | C2 |

Tables 6 and 7 show that inclusion of 5% ethanol compared to the same system without ethanol provides similar microemulsion region sizes for both placebo systems (20% to 50% oil) and the corresponding 100 mg/ml CyA systems.

TABLE 7

| K85EE % | Labrasol % | Cremophor RH40:Tween 80 (2:1) % | Ethanol % | CyA mg/ml | Clarity |
|---|---|---|---|---|---|
| 42.5 | 10 | 47.5 | n/a | 100 | C1/C2 |
| 44 | 6 | 51 | n/a | 100 | C1/C2 |
| 46 | 5 | 49 | n/a | 100 | C1/C2 |
| 46.5 | 11.5 | 42 | n/a | 100 | C1/C2 |
| 47 | 0 | 53 | n/a | 100 | C1/C2 |
| 53 | 8 | 42 | n/a | 100 | C2/C3 |
| 42.5 | 10 | 47.5 | 5% | 100 | C1/C2 |
| 44 | 6 | 51 | 5% | 100 | C1/C2 |
| 46 | 5 | 49 | 5% | 100 | C1/C2 |
| 46.5 | 11.5 | 42 | 5% | 100 | C2 |
| 47 | 0 | 53 | 5% | 100 | C1/C2 |
| 53 | 8 | 42 | 5% | 100 | C2/C3 |

EXAMPLE 6

EPAX5000TG/Cremophor RH40/Labrasol

Samples were prepared according to Example 2 for the omega-3 fatty acid oil EPAX5000TG and a surfactant system comprising Labrasol and Cremophor RH40 with varying percentages for all three of these components. Table 8 charts the clarity values for this system (placebo) upon 1 to 20 dilution with water as well as 1 to 20 dilution clarity values for the corresponding systems in which 25, 50, 100 and 150 mg of CyA per ml of solution were added.

TABLE 8

| EPAX5000TG % | Labrasol % | Cremophor RH40% | CyA mg/ml | Clarity |
|---|---|---|---|---|
| 5 | 62 | 33 | n/a | C1 |
| 10 | 15 | 75 | n/a | C1 |
| 12 | 45 | 43 | n/a | C1 |
| 15 | 79 | 6 | n/a | C4 |
| 20 | 38 | 42 | n/a | C1/C2 |
| 22 | 65 | 13 | n/a | C4 |
| 27 | 20 | 53 | n/a | C1/C2 |
| 30 | 56 | 14 | n/a | C4 |
| 5 | 62 | 33 | 25 | C1 |
| 10 | 15 | 75 | 25 | C1 |
| 12 | 45 | 43 | 25 | C1 |
| 20 | 36 | 42 | 25 | C1 |
| 20 | 27 | 53 | 25 | C1 |

TABLE 8-continued

| EPAX5000TG % | Labrasol % | Cremophor RH40% | CyA mg/ml | Clarity |
|---|---|---|---|---|
| 5 | 62 | 33 | 50 | C1 |
| 10 | 15 | 75 | 50 | C1 |
| 12 | 45 | 43 | 50 | C1 |
| 20 | 36 | 42 | 50 | C1 |
| 20 | 27 | 53 | 50 | C1 |
| 5 | 62 | 33 | 100 | C1 |
| 10 | 15 | 75 | 100 | C1 |
| 12 | 45 | 43 | 100 | C1 |
| 20 | 36 | 42 | 100 | C1 |
| 20 | 27 | 53 | 100 | C1 |
| 5 | 62 | 33 | 150 | C3 |
| 10 | 15 | 75 | 150 | C1 |
| 12 | 45 | 43 | 150 | C2 |
| 20 | 36 | 42 | 150 | C1 |
| 20 | 27 | 53 | 150 | C1 |

EXAMPLE 7

EPAX6000FA/Cremophor RH40/Labrasol

Samples were prepared according to Example 2 for the omega-3 fatty acid oil EPAX6000FA and a surfactant system comprising Labrasol and Cremophor RH40 with varying percentages for all three of these components. Table 9 charts the clarity values for this system (placebo) upon 1 to 20 dilution with water as well as 1 to 20 dilution clarity values for the corresponding systems in which 25, 50, 100 and 150 mg of CyA per ml of solution were added. From analysis of the placebo system, it appears that the greatest amount of oil possible in a microemulsion preconcentrate formulation formulated according to this system is around 27% EPAX6000FA.

TABLE 9

| EPAX6000FA % | Labrasol % | Cremophor RH40% | CyA mg/ml | Clarity |
|---|---|---|---|---|
| 5 | 62 | 33 | n/a | C1 |
| 10 | 15 | 75 | n/a | C1/C2 |
| 12 | 45 | 43 | n/a | C1/C2 |
| 15 | 79 | 6 | n/a | C2 |
| 20 | 38 | 42 | n/a | C2 |
| 22 | 65 | 13 | n/a | C4 |
| 27 | 20 | 53 | n/a | C2 |
| 30 | 56 | 14 | n/a | C4 |
| 40 | 5 | 55 | n/a | C2/C3 |
| 50 | 5 | 45 | n/a | C4 |
| 55 | 10 | 35 | n/a | C4 |
| 50 | 20 | 30 | n/a | C4 |
| 40 | 32 | 28 | n/a | C4 |
| 5 | 62 | 33 | 25 | C1 |
| 10 | 15 | 75 | 25 | C1 |
| 12 | 45 | 43 | 25 | C1 |
| 15 | 79 | 6 | 25 | C4 |
| 20 | 38 | 42 | 25 | C2 |
| 22 | 65 | 13 | 25 | C4 |
| 27 | 20 | 53 | 25 | C2 |
| 5 | 62 | 33 | 50 | C1 |
| 10 | 15 | 75 | 50 | C1 |
| 12 | 45 | 43 | 50 | C1 |
| 15 | 79 | 6 | 50 | C4 |
| 20 | 38 | 42 | 50 | C1 |
| 22 | 65 | 13 | 50 | C4 |
| 27 | 20 | 53 | 50 | C2 |
| 5 | 62 | 33 | 100 | C4 |
| 10 | 15 | 75 | 100 | C1 |
| 12 | 45 | 43 | 100 | C1 |
| 15 | 79 | 6 | 100 | C4 |
| 20 | 38 | 42 | 100 | C2 |
| 22 | 65 | 13 | 100 | C4 |
| 27 | 20 | 53 | 100 | C3 |

TABLE 9-continued

| EPAX6000FA % | Labrasol % | Cremophor RH40% | CyA mg/ml | Clarity |
|---|---|---|---|---|
| 5 | 62 | 33 | 150 | C4 |
| 10 | 15 | 75 | 150 | C2 |
| 12 | 45 | 43 | 150 | C3 |
| 15 | 79 | 6 | 150 | C4 |
| 20 | 38 | 42 | 150 | C3 |
| 22 | 65 | 13 | 150 | C4 |
| 27 | 20 | 53 | 150 | C3 |

EXAMPLE 8
K85TG/Cremophor RH40/Tween 80/Labrasol

Samples were prepared according to Example 2 for the omega-3 fatty acid oil K85TG and a surfactant system comprising Labrasol, Cremophor RH40 and Tween 80 (with Cremophor RH40 and Tween 80 held at a 2:1 ratio) with varying percentages for the oil, Labrasol and the Cremophor RH40 and Tween 80 mixture. Table 10 charts the clarity values for this system (placebo) upon 1 to 20 dilution with water. A pseudo-ternary phase diagram showing the microemulsion region (C1, C1/C2, and C2 clarity values) for this placebo system upon 1 to 20 dilution is shown in FIG. 1.

TABLE 10

| K85TG % | Labrasol % | Cremophor RH40: Tween 80 (2:1) % | CyA mg/ml | Clarity |
|---|---|---|---|---|
| 48.5 | 0 | 51.5 | n/a | C4 |
| 48.5 | 8.2 | 43.3 | n/a | C4 |
| 48.5 | 13.7 | 37.8 | n/a | C4 |
| 38.8 | 0 | 61.2 | n/a | C1/C2 |
| 38.8 | 9.9 | 51.4 | n/a | C3 |
| 38.8 | 16.2 | 45 | n/a | C4 |
| 31 | 0 | 69 | n/a | C2 |
| 31 | 11 | 58 | n/a | C2 |
| 31 | 16.4 | 50.6 | n/a | C4 |
| 21.7 | 0 | 78.3 | n/a | C1/C2 |
| 21.7 | 12.6 | 65.7 | n/a | C1/C2 |
| 21.7 | 20.8 | 57.5 | n/a | C1/C2 |
| 40 | 30 | 30 | n/a | C4 |
| 35 | 20 | 45 | n/a | C2 |
| 5 | 10 | 85 | n/a | C1 |
| 5 | 25 | 70 | n/a | C1 |
| 5 | 50 | 45 | n/a | C1 |
| 10 | 30 | 60 | n/a | C1 |
| 10 | 40 | 50 | n/a | C1/C2 |
| 15 | 10 | 75 | n/a | C1 |
| 15 | 15 | 70 | n/a | C2 |
| 15 | 60 | 25 | n/a | C1/C2 |
| 20 | 25 | 55 | n/a | C1/C2 |
| 25 | 35 | 40 | n/a | C4 |
| 25 | 45 | 30 | n/a | C2 |
| 35 | 20 | 45 | n/a | C2 |
| 40 | 30 | 30 | n/a | C4 |

Figure 2:
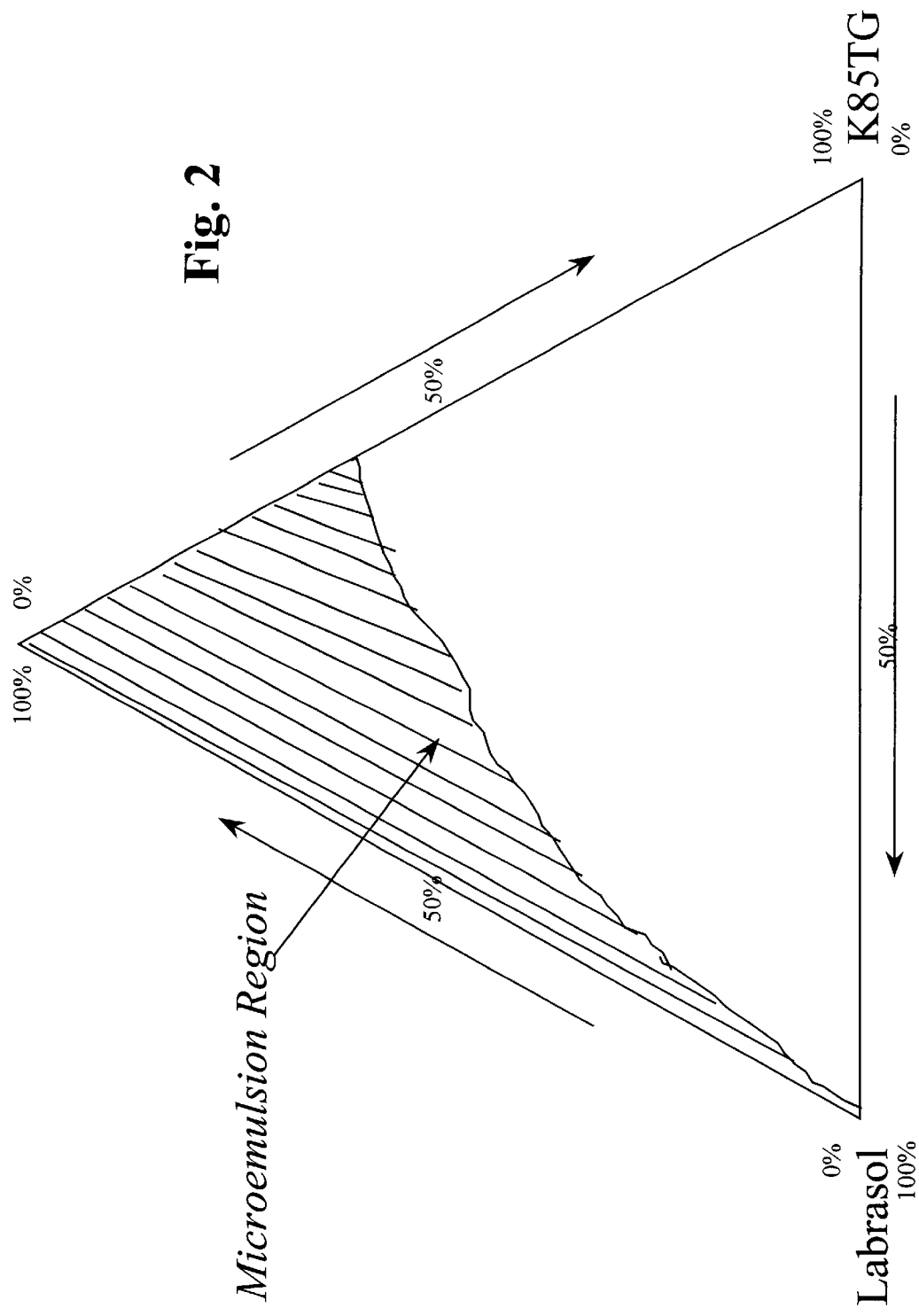
FIG. 2 shows a pseudo-ternary phase diagram for the 100 mg CyA system described in Example 8 upon a 1 to 20 dilution of the preconcentrate with water. The diagram plots the relative concentration of Labrasol (0 to 100%), the concentration of the omega-3 fatty acid oil K85TG (0 to 100%), and the concentration of Cremophor RH40: Tween 80 in a 2:1 ratio (0 to 100%) for compositions containing 100 mg CyA. The relative concentration of Labrasol increases from 0% at the lower right hand margin of the diagram to 100% at the lower left corner; the relative concentration of Cremophor RH40: Tween 80 in a 2:1 ratio increases from 0% at the baseline of the diagram to 100% at the apex; and the relative concentration of K85TG increases from 0% at the apex to 100% at the lower right hand corner of the diagram. The shaded area identifies those compositions having C1, C1/C2 or C2 clarity as the microemulsion region for a 1 to 20 dilution of the preconcentrate with water.

Table 11 charts the 1 to 20 dilution clarity values for the corresponding systems in which 25, 50, 100 and 150 mg of CyA per ml of solution were added. The pseudo-ternary phase diagram given in FIG. 2 shows the microemulsion region for the system upon 1 to 20 dilution having 100 mg/ml CyA per ml of solution.

TABLE 11

| K85TG % | Labrasol % | Cremophor RH40: Tween 80 (2:1) % | CyA mg/ml | Clarity |
|---|---|---|---|---|
| 21.7 | 0 | 78.3 | 100 | C1 |
| 21.7 | 12.6 | 65.7 | 100 | C1 |
| 21.7 | 20.8 | 57.5 | 100 | C1/C2 |
| 31 | 0 | 69 | 100 | C1/C2 |
| 31 | 11 | 58 | 100 | C2 |
| 31 | 16.4 | 50.6 | 100 | C2/C3 |
| 38.8 | 0 | 61.2 | 100 | C1/C2 |
| 38.8 | 9.9 | 51.4 | 100 | C2/C3 |
| 38.8 | 16.2 | 45 | 100 | C3 |
| 48.5 | 0 | 51.5 | 100 | C3 |
| 48.5 | 8.2 | 43.3 | 100 | C3 |
| 48.5 | 13.7 | 37.8 | 100 | C4 |

EXAMPLE 9
K85TG/Cremophor RH40/Labrasol

Samples were prepared according to Example 2 for the omega-3 fatty acid oil K85TG and a surfactant system comprising Labrasol and Cremophor RH40 with varying percentages for all three of these components. Table 12 charts the clarity values for this system (placebo) upon 1 to 20 dilution with water as well as 1 to 20 dilution clarity values for the corresponding systems in which 25, 50, 100 and 150 mg of CyA per ml of solution were added. From an analysis of the placebo system, it appears that the greatest amount of oil possible in a microemulsion preconcentrate formulation formulated according to this system is around 27% K85TG.

The microemulsion region on a pseudo-ternary phase diagram obtained by plotting the data for the K85EE/Cremophor/Labrasol system provided in this example is similar to that for the corresponding EPAX5000TG system (Example 6) and the EPAX6000FA system (Example 7) over a range of 0 to 150 mg/ml CyA. The corresponding K85EE system (Example 3) appears to form a larger microemulsion region than the K85TG system.

TABLE 12

| K85TG % | Labrasol % | Cremophor RH40% | CyA mg/ml | Clarity |
|---|---|---|---|---|
| 5 | 62 | 33 | n/a | C1/C2 |
| 10 | 15 | 75 | n/a | C1 |
| 12 | 45 | 43 | n/a | C1 |
| 15 | 79 | 6 | n/a | C4 |
| 20 | 38 | 42 | n/a | C2/C3 |
| 22 | 65 | 13 | n/a | C4 |
| 27 | 20 | 53 | n/a | C2 |
| 30 | 56 | 14 | n/a | C4 |
| 5 | 62 | 33 | 25 | C1 |
| 10 | 15 | 75 | 25 | C1 |
| 12 | 45 | 43 | 25 | C1 |
| 20 | 38 | 42 | 25 | C2 |
| 20 | 27 | 53 | 25 | C1 |
| 5 | 62 | 33 | 50 | C1 |
| 10 | 15 | 75 | 50 | C1 |
| 12 | 45 | 43 | 50 | C1 |
| 20 | 38 | 42 | 50 | C2 |
| 20 | 27 | 53 | 50 | C1 |
| 5 | 62 | 33 | 100 | C1 |
| 10 | 15 | 75 | 100 | C1 |
| 12 | 45 | 43 | 100 | C1 |
| 20 | 38 | 42 | 100 | C2 |
| 20 | 27 | 53 | 100 | C1 |
| 5 | 62 | 33 | 150 | C2 |
| 12 | 45 | 43 | 150 | C3 |
| 20 | 38 | 42 | 150 | C3 |
| 27 | 20 | 53 | 150 | C1 |

EXAMPLE 10

Mixed Fish Oils/Cremophor RH40/Tween 80/Labrasol

Samples were prepared according to Example 2 for the systems containing a mixture of K85EE and EPAX6000FA and a surfactant system comprising Labrasol, Tween 80 and Cremophor RH40 with varying percentages as described in Table 13. Table 13 charts the clarity values for these systems (placebo) upon 1 to 20 dilution with water as well as 1 to 20 dilution clarity values for the corresponding systems in which 50 or 100 mg of CyA per ml of solution were added.

TABLE 13

| K85EE/ EPAX6000FA (2.5:1) % | Cremophor RH40/ Tween 80 (2:1) % | Labrasol % | Clarity (without CyA) | Clarity (with 100 mg CyA) | Clarity (with 50 mg CyA) |
|---|---|---|---|---|---|
| 21.7 | 65.7 | 12.6 | C1 | C1 | C1 |
| 31 | 58 | 11 | C1 | C1 | C1 |
| 38.8 | 61.2 | 0 | C1/C2 | C1/C2 | C2 |
| 38.8 | 51.4 | 9.9 | C1/C2 | C1/C2 | C1/C2 |
| 38.8 | 45 | 16.2 | C1/C2 | C1/C2 | C1/C2 |
| 48.5 | 51.5 | 0 | C2 | C2 | C3 |
| 48.5 | 43.3 | 8.2 | C2 | C2 | C2/C3 |
| 48.5 | 37.8 | 13.7 | C2 | C2 | C2/C3 |
| 50.9 | 49.1 | 0 | C3 | C3 | C3 |

| K85EE/ EPAX6000FA (5:1) % | Cremophor RH40/ Tween 80 (4:1) % | | | | |
|---|---|---|---|---|---|
| 40 | 55 | 5 | C2 | C1/C2 | C1 |
| 42.5 | 52.5 | 5 | C1/C2 | C1/C2 | C1 |
| 45 | 50 | 5 | C1/C2 | C1/C2 | C1 |
| 47 | 48 | 5 | C2 | C2 | C1/C2 |

| K85EE/ EPAX6000FA (5:1) % | Cremophor RH40/ Tween 80 (2:1) % | | | | |
|---|---|---|---|---|---|
| 40 | 55 | 5 | C1/C2 | C1/C2 | C1/C2 |
| 42.5 | 52.5 | 5 | C2 | C1/C2 | C1/C2 |
| 45 | 50 | 5 | C2 | C1/C2 | C2 |
| 47 | 48 | 5 | C2 | C2 | C2 |

EXAMPLE 11

Formulations

The following microemulsion preconcentrate formulations according to the instant invention were prepared as follows. The given amounts of cyclosporin, the given amounts of the oil containing omega-3 fatty acid oil, and the given amounts of the surfactant system were stirred until a homogeneous solution was formed. The resulting cyclosporin-containing composition was transferred to a machine for preparing soft capsules and then encapsulated according to conventional methods for producing soft capsules. These products were designed for daily administration, for example administration of 3–8 capsules daily, thus providing both a therapeutically effective amount of the therapeutic agent cyclosporin A (300–800 mg for Formulations 1 and 2 or 75–200 mg cyclosporin A for Formulation 3) and a pharmaceutically effective amount of an omega-3 fatty acid oil (1.03–2.74 g EPA+DHA for Formulations 1 and 3 or 1.39–3.70 g EPA+DHA for Formulation 2) per day. Formulation 4 contains a mixture of omega-3 fatty acid oils as well as minor amounts of a hydrophilic solvent system. Of course, a daily dose may contain combinations of capsules having differing therapeutic agent and/or omega-3 fatty acid oil amounts such as the capsules of Formulations 1, 2, 3 and 4.

| Component | % (wt) of placebo system | wt/capsule |
|---|---|---|
| Formulation 1 | | |
| Oil Component: | | |
| K85EE | 37% | 407 mg (343 mg EPA + DHA) |
| Surfactant system: | | |
| Cremophor RH40 and Tween 80 (2:1) | 53% | 583 mg |
| Labrasol | 10% | 110 mg |
| Cyclosporin A | | 100 mg |
| | | 1200 mg total |
| Formulation 2 | | |
| Oil Component: | | |
| K85EE | 50% | 550 mg (462 mg EPA + DHA) |
| Surfactant system: | | |
| Cremophor RH40 and Tween 80 (2:1) | 40% | 440 mg |
| Labrasol | 10% | 110 mg |
| Cyclosporin A | | 100 mg |
| | | 1200 mg total |
| Formulation 3 | | |
| Oil Component: | | |
| K85EE | 37% | 407 mg (343 mg EPA + DHA) |
| Surfactant system: | | |
| Cremophor RH40 and Tween 80 (2:1) | 53% | 583 mg |
| Labrasol | 10% | 110 mg |
| Cyclosporin A | | 25 mg |
| | | 1125 mg total |

| Formulation 4 | | |
|---|---|---|
| Component | % (wt) of system | wt/capsule |
| Oil component: | | |
| K85EE and EPAX6000FA (2:1) | 37.05% | 407.55 mg |
| Surfactant system: | | |
| Cremophor RH40 and | 49.05% | 539.55 mg |

EXAMPLE 12

Formulations Containing Hydrophilic Solvent Systems

Preconcentrate formulations containing omega-3 fatty acid oil, a surfactant system and more than minor amounts of a hydrophilic solvent system are specified in Table 15. Clarity values for 1 to 50 dilutions of these formulations in a mixture of water and simulated gastric fluid (1:1) are given in Table 15.

TABLE 15

| | Formulation 13 | | Formulation 14 | | Formulation 15 | | Formulation 16 | |
|---|---|---|---|---|---|---|---|---|
| | mg/cap | % | mg/cap | % | mg/cap | % | mg/cap | % |
| Therapeutic Agent | | 7.0% | | 7.8% | | 7.6% | | 7.4% |
| Cyclosporin A | 50 | | 50 | | 50 | | 50 | |
| Oil Component | | 21.1% | | 23.3% | | 22.9% | | 22.1% |
| EPAX6000FA | 50 | | 50 | | 50 | | 50 | |
| K85EE | 100 | | 100 | | | | | |
| K85TG | | | | | 100 | | 100 | |
| Surfactant System | | 51.5% | | 51.1% | | 50.4% | | 48.5% |
| Labrasol | 90 | | 75 | | 75 | | 100 | |
| Myrj-52 | 130 | | 100 | | 100 | | 75 | |
| Tween 80 | 75 | | 80 | | 80 | | 80 | |
| Vitamin E-TPGS | 70 | | 75 | | 75 | | 75 | |
| Hydrophilic Solvent System | | 20.4% | | 17.8% | | 19.1% | | 22.1% |
| Ethanol | 50 | | 40 | | 50 | | 50 | |
| 1,2 Propylene Glycol | 95 | | 75 | | 75 | | 100 | |
| Clarity | C1 | | C1 | | C2 | | C2 | |

-continued

| Formulation 4 | | |
|---|---|---|
| Component | % (wt) of system | wt/capsule |
| Tween 80 (2:1) Labrasol | 9.35% | 102.85 mg |
| Hydrophilic Solvent System Ethanol | 4.55% | 50.05 mg |
| Cyclosporin A | | 100.00 mg |
| | | 1200 mg total |

Additional microemulsion preconcentrate formulations according to the instant invention were also prepared as given below in Table 14. The amount of Cyclosporin A present is given as mg per 1.1 of the preconcentrate (placebo) and the amount of the other components are given as a weight percentage of the preconcentrate (placebo).

TABLE 14

| Formulation No. | 5 | 6 | 7 | 8 | 9 | 10 | 11 | 12 |
|---|---|---|---|---|---|---|---|---|
| Cyclosporin A | 25 | 25 | 25 | 100 | 25 | 100 | 25 | 100 |
| K85EE | 37 | | | | | | | |
| K80EE | | 37 | 37 | 37 | 37 | 37 | 37 | 37 |
| Cremophor RH40 | 35.33 | 35.33 | 38.67 | 35.33 | 38.7 | 38.7 | 35.3 | 35.3 |
| Tween 80 | 17.67 | 17.67 | 19.33 | 17.67 | 19.3 | 19.3 | 17.7 | 17.7 |
| Labrasol | 10 | 5 | | 5 | | | | |
| Imwitor 375 | | | | | 5 | 5 | 5 | 5 |
| Ethanol | | 5 | 5 | 5 | | | 5 | 5 |

Additional preconcentrate formulations containing omega-3 fatty acid oil, a surfactant system and more than minor amounts of a hydrophilic solvent system are given below as Formulations 17 and 18.

| | Formulation 17 | |
|---|---|---|
| Component | % (wt) of system | wt/capsule |
| Oil component: | | |
| K85EE | 5.9% | 50 mg |
| EPAX6000FA | 11.8% | 100 mg |
| Surfactant system: | | |
| Tween 20 | 27.9% | 237.5 mg |
| Tween 80 | 27.9% | 237.5 mg |
| Hydrophilic Solvent System | | |
| Ethanolic NaOH (800 mg NaOH in 12 ml EtOH) | 20.6%* | 175 mg |
| Cyclosporin A | 5.9% | 50 mg |
| | | 850 mg total |

*0.3% EtOH

| Formulation 18 | | |
| --- | --- | --- |
| Component | % (wt) of system | wt/capsule |
| Oil component: | | |
| EPAX5000TG | 8.3% | 100 mg |
| EPAX6000FA | 16.5% | 50 mg |
| Surfactant system: | | |
| Tween80 | 12.0% | 72.7 mg |
| Glycerox 767 | 19.2% | 116.4 mg |
| Vitamin E-TPGS | 12.8% | 77.3 mg |
| Hydrophilic Solvent System | | |
| Ethanol | 11.7% | 70.9 mg |
| Ethanolic NaOH (66.7 mg NaOH in 1 ml EtOH) | 11.3% | 68.2 mg |
| Cyclosporin A | 8.3% | 50 mg |
| | | 605.5 mg |

Formulations containing fenofibrate, a potent lipid modulator agent, were prepared by mixing the omega-3 fatty acid oil component with the drug powder followed by the addition of the surfactant system and hydrophilic solvent system. The compositions may be prepared at room temperature or heated to 40–50° C. to accelerate the solubilization process. Several mixing techniques can be used ranging from mechanical stirring and agitation to sonication. The fenofibrate composition shown below provides a liquid or semi-solid preconcentrate at room temperature.

In vitro testing of the preconcentrates was carried out by diluting the preconcentrate in 50–100 fold water or simulated gastric fluid with gentle mixing or shaking. The aqueous medium temperature varied between 20 and 37° C. Particle size analysis was then carried out using a Nicomp 370. Data reported for Formulation 19 below corresponds to volume weighted distributions.

| Formulation 19 | |
| --- | --- |
| Component | Quantity (mg) |
| Oil component: | |
| EPAX4510 TG | 189 |
| EPAX6000 FA | 95 |
| Surfactant system: | |
| Tween 80 | 136 |
| Myrj 52 | 236 |
| Vitamin E-TPGS | 164 |
| Labrasol | 127 |
| Hydrophilic Solvent System | |
| Ethanol | 91 |
| 1,2-propylene glycol | 182 |
| Fenofibrate (mean particle size: 20 nm) | 100 |

EXAMPLE 13
Evaluation of Oral Bioavailability

A two period, two treatment randomised crossover study was designed. Ten (10) healthy male volunteers were recruited into the study and the following treatments were administered during the study: Formulation 5 (25 mg Cyclosporine) and Neoral® (Novartis) (25 mg Cyclosporine). Both treatments were dosed as four 25 mg capsules giving a total dose of 100 mg cyclosporine. Nine (9) subjects successfully completed both treatment periods of this study. Table 16 summarises the mean primary pharmacokinetic parameters for the two treatments.

The results of this study showed that the microemulsion Formulation 5 had a relative bioavailability of 0.81 compared to Neoral® with significantly lower peak cyclosporine blood concentrations. Visual inspection of the individual plots suggested that the initial rate of cyclosporine absorption was slower following administration of the omega-3 oil product.

TABLE 16

| Parameter | Formulations 5 | Neoral capsules |
| --- | --- | --- |
| Cmax (ng/ml) | 392.76 ± 95.93 | 489.21 ± 98.08 |
| 90% Cl vs Neoral | 66–91 | |
| $AUC_{(0-t)}$ (ng/ml · hr) | 1083.44 ± 300.95 | 1346.92 ± 256.53 |
| 90% Cl vs Neoral | 72–86 | |
| $AUC_{(0-infinity)}$ (ng/ml · hr) | 1115.54 ± 302.74 | 1385.91 ± 244.50 |
| 90% Cl vs Neoral | 72–86 | |
| F ratio | 0.81 ± 0.16 | |

The combination of reduced peak blood concentrations along with the inclusion of the omega-3 oil in the microemulsion formulation may result in a reduction of the nephrotoxic side effects of cyclosporine. The relative bioavailability of approximately 80% of Neoral® for this formulation is considerably higher than that reported for the Sandimmun® cyclosporine formulation.

Stability evaluations were undertaken for Formulation 5 at 25° C. and 60% relative humidity as well as 40° C. and 75% relative humidity. No crystallization occurred under either of these conditions for Formulation 5 through 14 weeks. Upon dilution of the these preconcentrates, the clarity of the resulting microemulsions remained C1/C2.

A second biostudy was undertaken to evaluate the oral bioavailability of Formulations 6, 7 and 8 compared to Neoral Oral Solution (100 mg). The formulations were packaged in vials and diluted with orange juice prior administration Ten human subjects completed the study which consisted of four treatment periods.

Table 17 summarises the primary PK parameters for each of the four products administered during the study.

TABLE 17

| Parameter | Formulation 6 | Formulation 7 | Formulation 8 | Neoral Solution |
| --- | --- | --- | --- | --- |
| Cmax (ng/ml) | 313.86 ± 68.96 | 312.86 ± 73.25 | 335.97 ± 47.38 | 472.31 ± 89.00 |
| $AUC_{(0-24\,h)}$ (ng/ml · hr) | 1063.30 ± 301.27 | 1042.96 ± 306.84 | 1068.85 ± 258.50 | 1523.20 ± 313.73 |
| $AUC_{(0-infinity)}$ (ng/ml · hr) | 1123.61 ± 323.66 | 1111.52 ± 333.47 | 1121.44 ± 276.67 | 1595.80 ± 335.58 |
| F ratio* | 71.3 ± 19.1 | 70.2 ± 17.9 | 72.1 ± 21.5 | |

*based on $AUC_{(0-infinity)}$ data

All three products showed very similar bioavailabilities relative to Neoral Solution, approximately 71%. These three products produced good microemulsions of C1/C2 clarity on dilution 1 in 20 with deionized water. The mean particle size of these microemulsions was determined to be 38.7±0.3 nm, 39.1±0.1 nm and 39.1±0.4 nm (intensity weighted) for Formulation 6, 7 and 8, respectively.

What is claimed is:

1. A self-emulsifying preconcentrate pharmaceutical composition capable of forming an oil-in-water microemulsion or emulsion upon dilution with an aqueous solution, comprising:
   a) a pharmaceutically effective amount of an omega-3 fatty acid oil;
   b) a therapeutically effective amount of a poorly water soluble therapeutic agent, wherein the poorly water soluble therapeutic agent is substantially soluble in the omega-3 fatty acid oil; and
   c) a surfactant system comprising at least one surfactant; wherein the composition contains minor amounts or is substantially free of a hydrophilic solvent system.

2. The composition of claim 1, wherein the composition is a microemulsion preconcentrate.

3. The composition of claim 1, wherein the composition is an emulsion preconcentrate.

4. The composition of claim 1, wherein the composition is adapted for oral administration.

5. The composition of claim 1, wherein the omega-3 fatty acid oil is present in an amount ranging from 5 to 70% by weight.

6. The composition of claim 1, wherein the therapeutic agent is a cyclosporin.

7. The composition of claim 1, wherein the omega-3 fatty acid oil comprises an omega-3 fatty acid oil selected from the group consisting of eicosapentaenoic acid, salts of eicosapentaenoic acid, docosahexaenoic acid, salts of docosahexaenoic acid, triglycerides of eicosapentaenoic acid, triglycerides of docosahexaenoic acid, ethyl esters of eicosapentaenoic acid, ethyl esters of docosahexaenoic acid and mixtures thereof.

8. The composition of claim 1, wherein the omega-3 fatty acid oil comprises a component of a fish oil or a mixture of fish oils.

9. The composition of claim 8, wherein the omega-3 fatty acid component of the fish oil or the mixture of fish oils is at least 50% by weight.

10. The composition of claim 8, wherein the omega-3 fatty acid component of the fish oil or the mixture of fish oils is at least 70% by weight.

11. The composition of claim 8, wherein the omega-3 fatty acid component of the fish oil or the mixture of fish oils is at least 80% by weight.

12. The composition of claim 1, wherein the omega-3 fatty acid oil comprises omega-3 fatty acid triglycerides.

13. The composition of claim 1, wherein the omega-3 fatty acid oil comprises omega-3 fatty acid ethyl esters.

14. The composition of claim 1, wherein the therapeutic agent is selected from the group consisting of an analgesic, anti-allergic agent, anti-fungal, anti-inflammatory agent, anti-arrythmic agent, antibiotic, anticoagulant, antidepressant, antidiabetic agent, anti-epilepsy agent, antihypertensive agent, anti-gout agent, anti-malarial, antimigraine agent, antimuscarinic agent, antineoplastic agent, anti-protozoal agent, anxiolytic, thyroid, anti-thyroid, antiviral, anoretic, bisphosphonate, cardiac inotropic agent, cardiovascular agent, corticosteroid, diuretic, dopaminergic agent, gastrointestinal agent, hemostatic, histamin receptor antagonist, hypnotic, immunosuppressant, kidney protective agent, lipid regulating agent, muscle relaxant, neuroleptic, neurotropic agent, opioid agonist and antagonist, parasympathomimetic, protease inhibitor, prostglandin, sedative, sex hormone, stimulant, sympathomimetic, vasodilator and xanthin or mixtures thereof.

15. The composition of claim 1, wherein the composition is adapted for topical administration.

16. The composition of claim 1, wherein the composition is adapted for parenteral administration.

17. A microemulsion or emulsion pharmaceutical composition comprising the self-emulsifying preconcentrate of claim 1 diluted with an aqueous solution.

18. The composition of claim 17, wherein the composition is a microemulsion.

19. The composition of claim 17, wherein the composition is an emulsion.

20. The composition of claim 17, wherein the composition is adapted for oral administration.

21. The composition of claim 17, wherein the therapeutic agent is a cyclosporin.

22. The composition of claim 17, wherein the omega-3 fatty acid oil comprises an omega-3 fatty acid oil selected from the group consisting of eicosapentaenoic acid, salts of eicosapentaenoic acid, docosahexaenoic acid, salts of docosahexaenoic acid, triglycerides of eicosapentaenoic acid, triglycerides of docosahexaenoic acid, ethyl esters of eicosapentaenoic acid, ethyl esters of docosahexaenoic acid and mixtures thereof.

23. The composition of claim 17, wherein the omega-3 fatty acid oil comprises a component of a fish oil or a mixture of fish oils.

24. The composition of claim 23, wherein the omega-3 fatty acid component of the fish oil or the mixture of fish oils is at least 50% by weight.

25. The composition of claim 23, wherein the omega-3 fatty acid component of the fish oil or the mixture of fish oils is at least 70% by weight.

26. The composition of claim 23, wherein the omega-3 fatty acid component of the fish oil or the mixture of fish oils is at least 80% by weight.

27. The composition of claim 17, wherein the therapeutic agent is selected from the group consisting of an analgesic, anti-allergic agent, anti-fungal, anti-inflammatory agent, anti-arrythmic agent, antibiotic, anticoagulant, antidepressant, antidiabetic agent, anti-epilepsy agent, antihypertensive agent, anti-gout agent, anti-malarial, antimigraine agent, antimuscarinic agent, antineoplastic agent, anti-protozoal agent, anxiolytic, thyroid, anti-thyroid, antiviral, anoretic, bisphosphonate, cardiac inotropic agent, cardiovascular agent, corticosteroid, diuretic, dopaminergic agent, gastrointestinal agent, hemostatic, histamine receptor antagonist, hypnotic, immunosuppressant, kidney protective agent, lipid regulating agent, muscle relaxant, neuroleptic, neurotropic agent, opioid agonist and antagonist, parasympathomimetic, protease inhibitor, prostglandin, sedative, sex hormone, stimulant, sympathomimetic, vasodilator and xanthin or mixtures thereof.

28. The composition of claim 17, wherein the omega-3 fatty acid oil comprises omega-3 fatty acid triglycerides.

29. The composition of claim 17, wherein the omega-3 fatty acid oil comprises omega-3 fatty acid ethyl esters.

30. The composition of claim 17, wherein the composition is adapted for topical administration.

31. The composition of claim 17, wherein the composition is adapted for parenteral administration.

32. The composition of claim 17, wherein the amount of aqueous solution to preconcentrate is 1:1 or greater.

33. A method of lowering the therapeutically effective amount of a poorly water soluble therapeutic agent comprising administering to a human in need of a therapeutically effective amount of the therapeutic agent the self-emulsifying preconcentrate of claim 1, wherein the omega-3 fatty acid oil exerts an additive effect or synergistic effect to the therapeutic effect of the therapeutic agent.

34. A method of reducing the side effects of a poorly water soluble therapeutic agent comprising administering to a human in need of a therapeutically effective amount of the therapeutic agent the self-emulsifying preconcentrate of claim 1, wherein the omega-3 fatty acid oil mediates at least one negative side effect of the therapeutic agent.

35. A method of lowering the therapeutically effective amount of a poorly water soluble therapeutic agent comprising administering to a human in need of a therapeutically effective amount of the therapeutic agent the microemulsion or emulsion of claim 17, wherein the omega-3 fatty acid oil exerts an additive effect or synergistic effect to the therapeutic effect of the therapeutic agent.

36. A method of reducing the side effects of a poorly water soluble therapeutic agent comprising administering to a human in need of a therapeutically effective amount of the therapeutic agent the microemulsion or emulsion of claim 17, wherein the omega-3 fatty acid oil mediates at least one negative side effect of the therapeutic agent.

37. The method according to any of claims 33, 34, 35 or 36, wherein the poorly water soluble therapeutic agent is a cyclosporin.

38. A hard or softgel capsule formulation comprising the composition of claim 1.

39. A self-emulsifying preconcentrate pharmaceutical composition capable of forming an oil-in-water microemulsion or emulsion upon dilution with an aqueous solution, comprising:
   a) a pharmaceutically effective amount of an omega-3 fatty acid oil;
   b) a therapeutically effective amount of a poorly water soluble therapeutic agent, wherein the poorly water soluble therapeutic agent is substantially soluble in the omega-3 fatty acid oil; and
   c) a surfactant system comprising at least one surfactant.

* * * * *